US008420235B2

(12) United States Patent
Zheng (10) Patent No.: US 8,420,235 B2
(45) Date of Patent: Apr. 16, 2013

(54) EMISSIVE DIARYL ACETYLENES

(75) Inventor: Shijun Zheng, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 397 days.

(21) Appl. No.: 12/788,535

(22) Filed: May 27, 2010

(65) Prior Publication Data

US 2010/0308716 A1 Dec. 9, 2010

Related U.S. Application Data

(60) Provisional application No. 61/184,110, filed on Jun. 4, 2009.

(51) Int. Cl.
*H01L 51/54* (2006.01)
*C07C 255/54* (2006.01)

(52) U.S. Cl.
USPC .......... 428/690; 428/917; 313/504; 313/506; 558/423; 558/424

(58) Field of Classification Search .................. None
See application file for complete search history.

(56) References Cited

U.S. PATENT DOCUMENTS

| | | | |
|---|---|---|---|
| 4,769,384 A | 9/1988 | Kise et al. | |
| 5,847,797 A * | 12/1998 | Van Dijk | 349/158 |
| 6,210,814 B1 | 4/2001 | Thompson et al. | |
| 6,517,958 B1 | 2/2003 | Sellinger et al. | |
| 6,805,920 B2 * | 10/2004 | Nakano et al. | 428/1.1 |
| 6,872,477 B2 | 3/2005 | Thompson et al. | |
| 7,250,226 B2 | 7/2007 | Tokito et al. | |
| 2006/0006363 A1 | 1/2006 | Heckmeier et al. | |
| 2006/0050354 A1 | 3/2006 | Heckmeier et al. | |
| 2008/0135804 A1 | 6/2008 | Qiu et al. | |
| 2008/0269486 A1 | 10/2008 | Zhang-Lin | |
| 2010/0308310 A1 | 12/2010 | Zheng et al. | |

FOREIGN PATENT DOCUMENTS

| | | |
|---|---|---|
| CN | 1 293 180 A | 5/2001 |
| DE | 10241301 | 3/2004 |
| DE | 10253325 | 5/2004 |
| DE | 10253606 | 5/2004 |
| GB | 1 469 818 A | 4/1977 |
| GB | 2 367 057 A | 3/2002 |
| JP | 5286920 | 11/1993 |
| JP | 10-340786 A | 12/1998 |
| JP | 8-184865 A | 5/2001 |
| JP | 2002-096558 A | 4/2002 |
| JP | 2002-308832 | 10/2002 |
| WO | WO 01/06240 | 1/2001 |
| WO | WO 02/093244 A2 | 11/2002 |
| WO | WO 2004/046805 | 6/2004 |

OTHER PUBLICATIONS

Journal of Fluorine Chemistry, (1991), 52(3), pp. 333-340.*
"Photorefractive polymer composites with short response times.", Journal of Imaging Science and Technology (1999), 43(5), 405-412.
"Photorefractive polymers sensitized by two-photon absorption.", Optics Letters (2002), 27(1), 19-21.
"Photorefractive polymers with non-destructive readout.", Advanced Functional Materials (2002), 12(9), 615-620.
"Polymers for holographic imaging and displays. ", Polymer Preprints (American Chemical Society, Division of Polymer Chemistry) (2002), 43(1), 158-159.
Copending U.S. Appl. No. 12/787,753, filed May 26, 2010.
Copending U.S. Appl. No. 12/825,953, filed Jun. 29, 2010.
Copending U.S. Appl. No. 12/826,589, filed Jun. 29, 2010.
International Search Report and Written Opinion in PCT/US2010/037301, dated Aug. 4, 2010.
International Preliminary Report on Patentability in PCT/US2010/037301, dated Dec. 4, 2011.

* cited by examiner

*Primary Examiner* — Dawn L. Garrett
(74) *Attorney, Agent, or Firm* — Knobbe Martens Olson & Bear, LLP (57) ABSTRACT

Disclosed herein are compounds represented by a formula:

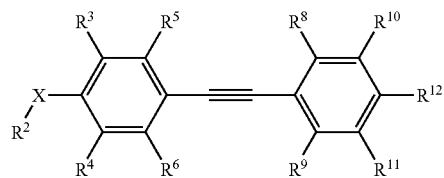

Compositions and light-emitting devices related thereto are also disclosed.

15 Claims, 4 Drawing Sheets

EMISSIVE DIARYL ACETYLENES

CROSS-REFERENCE TO RELATED APPLICATIONS

This application claims the benefit of U.S. Provisional Application No. 61/184,110, filed Jun. 4, 2009, which is incorporated by reference herein in its entirety.

BACKGROUND

1. Field of the Invention

This invention relates to light-emitting compounds or compositions and light-emitting devices that include the light-emitting compounds or compositions.

2. Description of the Related Art

Organic light-emitting devices (OLEDs) have been widely developed for flat panel displays, and are moving fast towards solid state lighting (SSL) applications. Organic Light Emitting Diodes (OLEDs) comprise a cathode, a hole transporting layer, an emissive layer, an electron transporting layer, and an anode. Light emitted from an OLED device is the result of recombination of positive charges (holes) and negative charges (electrons) inside an organic (emissive) layer. The holes and electrons combine within a single molecule or a small cluster of molecules to generate excitons, which are molecules in an excited state, or groups of organic molecules bound together in an excited state. When the organic molecules release the required energy and return to its stable state, photons are generated. The organic compound or group of compounds which emit the photons is referred as an electro-fluorescent material or electro-phosphorescent material depending on the nature of the radiative process. Thus the OLED emissive compounds may be selected for their ability to absorb primary radiation and emit radiation of a desired wavelength. For blue emitters, for example, emission within principle emission bands of 440 to 490 nm is desirable.

SSL applications may require white OLED device to achieve greater than 1,500 μm brightness, a color rendering index (CRI) greater than 70, and an operating time greater than 100,000 hours at 1,000 μlm/w. There are many approaches for generating white light from an OLED, but two common approaches are: direct combination of red, blue, and green light using either lateral patterning or vertical stacking of three emitters; and partial down conversion of blue light in combination with yellow phosphors. Both of these common approaches may be more effective if a highly efficient chemical- and photo-stable blue dye is employed. However, blue emitters may be less stable than dyes which emit other colors. Furthermore, and there are very few blue emitting devices showing CIE y value below 0.2 yet still with respectable efficiency. Thus, the development of deep blue emitters with good stability and high luminescence efficiency is desirable to effectively reduce power consumption and generating emission of different colors.

Diphenyl acetylene compounds have been used as additives in organic photoreflective polymer composites for electrooptic, photorefractive and liquid crystal applications (see for example, US 2006/0050354 and US 2006/000363). Thompson, et al (U.S. Pat. No. 6,210,814) described a polarization dopant molecule that contributed to the local dipole moment to spectrally shift the emission of a separate emissive dopant. Thompson, et al (U.S. Pat. No. 6,045,930) describes a [tris-diphenylacetylene amine] compound However, none of these compounds were described as blue emitting fluorescent compounds. Thus, the development of deep blue emitters with good stability and high luminescence efficiency is desirable to effectively reduce power consumption and generating emission of different colors.

SUMMARY OF THE INVENTION

One embodiment provides compounds that are useful as deep blue emitters. These compounds are represented by a formula:

(Formula 1)

wherein $R^2$ is $C_{1-30}$ alkyl, or $C_{1-30}O_{1-15}$ ether; $R^3$, $R^4$, $R^5$, and $R^6$ are independently selected from —H, —F, —Cl, —Br, —I, $C_{1-10}$ alkyl, $C_{1-10}O$ ether, and optionally substituted $C_{6-10}$ aryl; X is —O— or —$NR^7$—, wherein $R^7$ is —H, $C_{1-12}$ alkyl, or $C_{1-12}O_{1-6}$ ether; $R^8$ and $R^9$ are independently —H, —F, —Cl, —Br, —I, $C_{1-10}$ alkyl or $C_{1-10}$ ether; and $R^{10}$, $R^{11}$ and $R^{12}$ are independently halogen, —CN, or —$NO_2$.

Another embodiment is a light-emitting device, comprising an anode layer; a cathode layer; and a light-emitting layer positioned between, and electrically connected to, the anode layer and the cathode layer, the light-emitting layer comprising a compound disclosed herein.

DETAILED DESCRIPTION OF THE PREFERRED EMBODIMENTS

Reference to a compound also includes any salts of that compound.

Unless otherwise indicated, when a structural feature such as alkyl or aryl is referred to as being "optionally substituted," it is meant that the feature may have no substituents or may have one or more substituents. A feature that is "substituted" has one or more substituents. In some embodiments, each substituent is composed of 0-20 carbon atoms, 0-47 hydrogen atoms, 0-5 oxygen atoms, 0-2 sulfur atoms, 0-3 nitrogen atoms, 0-1 silicon atoms, 0-7 fluorine atoms, 0-3 chlorine atoms, 0-3 bromine atoms, and 0-3 iodine atoms. Examples include, but are not limited to, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, the term "aryl" refers to an aromatic ring or ring system. Exemplary aryl groups are phenyl, naphthyl, etc.

As used herein, the term "$C_{6-10}$ aryl" refers to aryl where the ring or ring system has from 6-10 carbon atoms. "$C_{6-10}$ aryl" does not characterize or limit any hydrogen or substituents attached to the ring atoms.

As used herein, the term "heteroaryl" refers to an aromatic ring or ring system having one or more atoms selected from nitrogen, oxygen, or sulfur in an aromatic ring. Examples include pyridinyl, pyridazinyl, triazinyl, pyridinyl, pyrimidinyl, pyrazinyl, benzoimidazolyl, indolyl, benzooxazolyl, etc.

As used herein, the term "$C_{3-10}O_{0-1}N_{1-3}$ heteroaryl" refers to heteroaryl where the atoms of the ring or ring system has from 3-10 carbon atoms, from 0-1 oxygen atoms, and from 1-3 nitrogen atoms. "$C_{3-10}O_{0-1}N_{1-3}$ heteroaryl" does not characterize or limit any hydrogen or substituents attached to the ring atoms.

As used herein, the term "alkyl" refers to a moiety consisting of carbon and hydrogen containing no double or triple bonds. Alkyl may be linear, branched, cyclic, or a combination thereof, and contain from one to thirty-five carbon atoms. Examples of alkyl groups include but are not limited to methyl, ethyl, propyl, isopropyl, cyclopropyl, n-butyl, isobutyl, tert-butyl, cyclobutyl, pentyl isomers, cyclopentane, hexyl isomer, cyclohexane, and the like.

As used herein, the term "linear alkyl" refers to —$(CH_2)_q$CH$_3$, where q is 0-34.

As used herein, the term "$C_{1-30}$ alkyl" refers to alkyl having from 1 to 30 carbon atoms such as methyl, ethyl, propyl isomers, butyl isomers, cyclobutyl isomers, pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc., up to 30 carbon atoms.

As used herein, the term "$C_{1-12}$ alkyl" refers to alkyl having from 1 to 12 carbon atoms such as methyl, ethyl, propyl isomers, butyl isomers, cyclobutyl isomers, pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc., up to 12 carbon atoms.

As used herein, the term "$C_{1-10}$ alkyl" refers to alkyl having from 1 to 10 carbon atoms such as methyl, ethyl, propyl isomers, butyl isomers, cyclobutyl isomers, pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc.

As used herein, the term "ether" refers to a moiety consisting of carbon, hydrogen, and single bonded oxygen, i.e. —O—, provided that —O—O— is not present. Examples include: —O-alkyl, such as —O-methyl, —O-ethyl, —O-propyl, —O-isopropyl, etc.; -alkyl-O-alkyl, such as -methyl-O-methyl, -methyl-O-ethyl, -methyl-O-isopropyl, etc.; and —$(CH_2CH_2O)_n$—.

As used herein, the term "$C_{1-30}O_{1-15}$ ether" refers to ether having from 1-30 carbon atoms, from 1-15 oxygen atoms, and hydrogen. Examples include, but are not limited to, —$(CH_2CH_2O)_n$CH$_3$— where n is 1, 2, 3, 4, 5, 6, 7, 8, 9, 10, 11, 12, 13, or 14; —[CH(CH$_3$)CH$_2$O]$_n$CH$_3$— where n is 1, 2, 3, 4, 5, 6, 7, 8, or 9; and —$(CH_2)_o$—O—$(CH_2)_p$CH$_3$ where o+p is from 1-29.

As used herein, the term "$C_{1-10}O$ ether" refers to ether having from 1-10 carbon atoms, 1 oxygen atom, and hydrogen, such as: —O—$C_xH_{2x+1}$, or —$OC_xH_{2x}$, where x is 1-10, e.g. —O-methyl, —O-ethyl, —O—$C_3H_7$, —OC$_3$H$_6$, —OC$_4$H$_9$, —OC$_5$H$_{11}$, —O—O$_5$H$_{10}$, etc.

As used herein, the term "work function" of a metal refers to a measure of the minimum energy required to extract an electron from the surface of the metal.

As used herein, the term "high work function metal" refers to a metal or alloy that easily injects holes and typically has a work function greater than or equal to 4.5.

As used herein, the term "low work function metal" refers to a metal or alloy that easily loses electrons and typically has a work function less than 4.3.

A material is white light-emitting if it emits white light. White light is light having the approximate CIE color coordinates (X=⅓, Y=⅓). The CIE color coordinates (X=⅓, Y=⅓) is defined as the achromatic point. The X and Y color coordinates are weights applied to the CIE primaries to match a color. A more detailed description of these terms may be found in CIE 1971, International Commission on Illumination, Colorimetry: Official Recommendations of the International Commission on Illumination, Publication CIE No. 15 (E-1.3.1) 1971, Bureau Central de la CIE, Paris, 1971 and in F. W. Billmeyer, Jr., M. Saltzman, Principles of Color Technology, 2nd edition, John Wiley & Sons, Inc., New York, 1981, both of which are hereby incorporated by reference in their entireties. The color rendering index (CRI) refers to the ability to render various colors and has values ranging from 0 to 100, with 100 being the best.

A material is "deep blue" emitting if it emits deep blue light. Deep Blue light is light having the approximate CIE color coordinates X≦0.2 and Y≦0.1). Non-limiting examples include X=[0.14], Y=[0.08], or X=0.16 and Y=0.10 (CIE 1931).

Some embodiments provide compounds that are useful as deep blue emitters. The compounds are represented by a formula I:

(Formula 1)

wherein $R^2$ is $C_{1-30}$ alkyl, or $C_{1-30}O_{1-15}$ ether; $R^3$, $R^4$, $R^5$, and $R^6$ are independently selected from —H, —F, —Cl, —Br, —I, $C_{1-10}$ alkyl, $C_{1-10}O$ ether, and optionally substituted $C_{6-10}$ aryl; X is —O— or —NR$^7$—, wherein $R^7$ is —H, $C_{1-12}$ alkyl, or $C_{1-12}O_{1-6}$ ether; $R^8$ and $R^9$ are independently —H, —F, —Cl, —Br, —I, $C_{1-10}$ alkyl or $C_{1-10}$ ether; and $R^{10}$, $R^{11}$ and $R^{12}$ are independently halogen, —CN, or —NO$_2$.

In some embodiments, if $R^2$ is methyl, ethyl, propyl, or isopropyl, at least one of $R^3$, $R^4$, $R^5$, and $R^6$ is not —H. In some embodiments, if $R^2$ is linear alkyl, at least one of $R^3$, $R^4$, $R^5$, and $R^6$ is not —H.

Some embodiments comprise blue emitting compounds characterized by substituted diphenyl acetylene compounds comprising electron donating substituents on one phenyl ring and electron withdrawing substituents on the other phenyl ring. Electron withdrawing groups and electron donating groups have the ordinary meaning used by one skilled in the art. In some embodiments, an electron withdrawing group is a moiety which is more electronegative than hydrogen, or alternatively, withdraws more electron density from the phenyl ring than hydrogen does. In some embodiments, an electron donating group is a moiety which is less electronegative than hydrogen, or alternatively, donates more electron density into the phenyl ring than hydrogen does.

While this invention is not limited by any particular theory or mechanism, it is believed that in some embodiments, a blue emitting compound may have a "push" (electron donating) end and a "pull" (electron-withdrawing or electron-accepting) end which affects the orbital structure of an emissive molecule to the extent that the energy levels of the molecule may shift from an ultraviolet emitting compound to a deep blue emitting compound. Thus in some embodiments, X of Formula 1, at the "push" end of the blue emitting compound, comprises an electron donating hetero-atom, N, O or S, or in a preferred embodiment an O or an N, or in a still more preferred embodiment an O at the "push" end. In another embodiment, the phenyl group proximal to the "push" end comprises electron donating groups for at least one, or alternatively all, of $R^3$, $R^4$, and $R^4$. In some embodiments, the electron donating group may be a methyl group, an isopropyl group, a phenyloxy group, a benzyloxy group, a dimethylamino group, a diphenylamino group, a pyrrolidine group, or a phenyl group. In some embodiments, at least one or alternatively all, of $R^{10}$, $R^{11}$ and $R^{12}$ at the "pull" end of the deep blue emitting compound, can independently be an electron withdrawing group, such as a fluoro group, a cyano group, a trifluoromethyl group, or a phenyl group with a trifluoromethyl moiety In some embodiments, $R^2$ may also be, but is not limited to, $C_{1-12}$ alkyl or $C_{4-30}$ alkyl. "$C_{4-30}$ alkyl" is alkyl having from 4 to 30 carbon atoms such as butyl isomers, cyclobutyl isomers, pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc., up to 30 carbon atoms.

In some embodiments, $R^2$ may also be, but is not limited to, $C_{1-9}O_{1-4}$ ether. "$C_{1-9}O_{1-4}$ ether" is ether having from 1-9 carbon atoms, 1-4 oxygen atoms, and hydrogen. Examples include, but are not limited to, —CH$_2$CH$_2$OCH$_3$, —CH$_2$CH$_2$OCH$_2$CH$_2$OCH$_3$, —CH$_2$CH(CH$_3$)OCH$_3$, —CH$_2$CH(CH$_3$)OCH$_2$CH(CH$_3$)OCH$_3$, —CH$_2$CH$_2$OCH$_2$CH$_2$OCH$_3$, —CH$_2$CH$_2$OCH$_2$CH$_2$OCH$_2$CH$_2$OCH$_3$, etc.

In some embodiments, $R^2$ is selected from the following group:

In some embodiments, if $R^2$ is methyl, ethyl, propyl, or isopropyl, at least one of $R^3$, $R^4$, $R^5$, and $R^6$ is not —H. In other words, if $R^2$ is methyl, ethyl, propyl, or isopropyl, then (1) $R^3$ is —F, —Cl, —Br, —I, $C_{1-10}$ alkyl, $C_{1-10}O$ ether, or optionally substituted $C_{6-10}$ aryl; and $R^4$, $R^5$, and $R^6$ are independently —H, —F, —Cl, —Br, —I, $C_{1-10}$ alkyl, $C_{1-10}O$ ether, or optionally substituted $C_{6-10}$ aryl; (2) $R^4$ is —F, —Cl, —Br, —I, $C_{1-10}$ alkyl, $C_{1-10}O$ ether, or optionally substituted $C_{6-10}$ aryl; and $R^3$, $R^5$, and $R^6$ are independently —H, —F, —Cl, —Br, —I, $C_{1-10}$ alkyl, $C_{1-10}O$ ether, or optionally substituted $C_{6-10}$ aryl; (3) $R^5$ is —F, —Cl, —Br, —I, $C_{1-10}$ alkyl, $C_{1-10}O$ ether, or optionally substituted $C_{6-10}$ aryl; and $R^3$, $R^4$, and $R^6$ are independently —H, —F, —Cl, —Br, —I, $C_{1-10}$ alkyl, $C_{1-10}O$ ether, and optionally substituted $C_{6-10}$ aryl; or (4) $R^6$ is —F, —Cl, —Br, —I, $C_{1-10}$ alkyl, $C_{1-10}O$ ether, and optionally substituted $C_{6-10}$ aryl; and $R^3$, $R^4$, and $R^5$ are independently —H, —F, —Cl, —Br, —I, $C_{1-10}$ alkyl, $C_{1-10}O$ ether, or optionally substituted $C_{6-10}$ aryl.

In some embodiments, $R^3$, $R^4$, $R^5$, and $R^6$ are independently selected from: —H, —CH$_3$, isopropyl, and —OCH$_3$. In some embodiments $R^5$ is —F, —Cl, —Br, —I, $C_{1-10}$ alkyl, $C_{1-10}O$ ether, or optionally substituted $C_{6-10}$ aryl. In some embodiments $R^5$ and $R^6$ are independently —F, —Cl, —Br, —I, $C_{1-10}$ alkyl, $C_{1-10}O$ ether, or optionally substituted $C_{6-10}$ aryl. In some embodiments, $R^5$ is —F, —Cl, —Br, —I, $C_{1-4}$ alkyl, or $C_{1-4}O$ ether. In some embodiments, $R^5$ and $R^6$ are independently —F, —Cl, —Br, —I, $C_{1-4}$ alkyl, or $C_{1-4}O$ ether. In some embodiments, $R^5$ is —CH$_3$, isopropyl, or —OCH$_3$.

In some embodiments, the deep blue emissive compound may be represented by the following formula:

(Formula 2)

wherein $X^1$ is —O(CH$_2$CH$_2$O)$_n$—C$_o$H$_{2o+1}$; n is 0, 1, 2, 3, or 4; o is 1, 2, 3, 4, 5, 6, 7, or 8; $R^3$, $R^4$, $R^5$, and $R^6$ are independently —H, $C_{1-4}$ alkyl, or $C_{1-4}O$-alkyl; and $R^8$ and $R^9$ are independently —H, —F, —Cl, —Br, or —I. In these embodiments, both the o subscript for C and the o which is part of the subscript for H are the same value.

Non-limiting examples of a compound of Formula I include:

-continued

Another embodiment described herein relates to a light emitting device that can include: an anode layer comprising a high work function metal; a cathode layer comprising a low work function metal; and a light-emitting layer positioned between, and electrically connected to, the anode layer and the cathode layer.

The compounds or compositions described herein can be incorporated into light-emitting devices in various ways. For example, an embodiment provides a light-emitting device, comprising: an anode layer comprising a high work function metal; a cathode layer comprising a low work function metal; and a light-emitting layer positioned between, and electrically connected to, the anode layer and the cathode layer. The light-emitting layer comprises the compounds or compositions disclosed herein.

An anode layer may comprise a conventional material such as a metal, mixed metal, alloy, metal oxide or mixed-metal oxide, or a conductive polymer. Examples of suitable metals include the Group 1 metals, the metals in Groups 4, 5, 6, and the Group 8-10 transition metals. If the anode layer is to be light-transmitting, mixed-metal oxides of Group 12, 13, and 14 metals or alloys thereof, such as Au, Pt, and indium-tin-oxide (ITO), may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In an embodiment, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In an embodiment, the cathode layer can have a thickness in the range of about 1 nm to about 1000 nm.

The amount of the compounds disclosed herein in the light-emitting composition can vary. In one embodiment, the amount of a compound disclosed herein in the light-emitting layer is from about 1% to about 100% by weight of the light-emitting layer. In another embodiment, the amount of a compound disclosed herein in the light-emitting layer is from about 1% to about 10% by weight of the light-emitting layer. In another embodiment, the amount of a compound disclosed herein in the light-emitting layer is about 3% by weight of the light-emitting layer.

The thickness of the light-emitting layer may vary. In one embodiment, the light-emitting layer has a thickness from about 20 nm to about 200 nm. In another embodiment, the light-emitting layer has a thickness in the range of about 20 nm to about 150 nm.

In another embodiment, the light-emitting layer may also be configured to emit blue light.

In some embodiments, the light-emitting layer can further include a host material. Exemplary host materials are known to those skilled in the art. For example, the host material included in the light-emitting layer can be an optionally substituted compound selected from: an aromatic-substituted amine, an aromatic-substituted phosphine, a thiophene, an oxadiazole, 2-(4-biphenylyl)-5-(4-tert-butylphenyl)-1,3,4-oxadiazole (PBD), 1,3-bis(N,N-t-butyl-phenyl)-1,3,4-oxadiazole (OXD-7), a triazole, 3-phenyl-4-(1'-naphthyl)-5-phenyl-1,2,4-triazole (TAZ), 3,4,5-Triphenyl-1,2,3-triazole, 3,5-Bis(4-tert-butyl-phenyl)-4-phenyl[1,2,4]triazole, an aromatic phenanthroline, 2,9-dimethyl-4,7-diphenyl-phenanthroline (bathocuproine or BCP), 2,9-Dimethyl-4,7-diphenyl-1,10-phenanthroline, a benzoxazole, a benzothiazole, a quinoline, aluminum tris(8-hydroxyquinolate) (Alq3), a pyridine, a dicyanoimidazole, cyano-substituted aromatic, 1,3,5-tris(2-N-phenylbenzimidazolyl)benzene (TPBI), 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4'-bis[N,N'-(3-tolyl)amino]-3,3'-dimethylbiphenyl (HMTPD), 1,1-Bis(4-bis(4-methylphenyl) aminophenyl)cyclohexane, a carbazole, 4,4'-N,N'-dicarbazole-biphenyl (CBP), poly(9-vinylcarbazole) (PVK), N,N'N"-1,3,5-tricarbazoloylbenzene (tCP), a polythiophene, a benzidine, N,N'-bis(4-butylphenyl)-N,N'-bis(phenyl)benzidine, a triphenylamine, 4,4',4"-Tris(N-(naphthylen-2-yl)-N-phenylamino)triphenylamine, 4,4',4"-tris(3-methylphenylphenylamino)triphenylamine (MTDATA), a phenylenediamine, a polyacetylene, and a phthalocyanine metal complex.

It is understood to those skilled in the art that the groups described above as possible hosts can function as hole-transport materials or electron-transport materials. In one embodiment, the light-emitting layer further comprises a hole-transport material or an electron-transport material.

Exemplary hole-transport materials include 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4',4''-tris(3-methylphenylphenylamino)triphenylamine (MTDATA), 4,4'-bis[N,N'-(3-tolyl)amino]-3,3'-dimethylbiphenyl (HMTPD), N,N'N''-1,3,5-tricarbazoloylbenzene (tCP), 4,4'-N,N'-dicarbazole-biphenyl (CBP), poly(9-vinylcarbazole) (PVK), 3,4,5-Triphenyl-1,2,3-triazole, 3,5-Bis(4-tert-butyl-phenyl)-4-phenyl[1,2,4]triazole, 2,9-Dimethyl-4,7-diphenyl-1,10-phenanthroline, 1,1-Bis(4-bis(4-methylphenyl)aminophenyl)cyclohexane, N,N'-bis(4-butylphenyl)-N,N'-bis(phenyl)benzidine, 4,4',4''-Tris(N-(naphthylen-2-yl)-N-phenylamino)triphenylamine, and copper phthalocyanine.

The amount of the hole transport material in the light-emitting layer is from about 1% to about 99% by weight, or alternatively, from about 30% to about 70% by weight, of the light-emitting layer.

If desired, additional layers may be included in the light-emitting device. Additional layers that may be included include an electron injection layer (EIL), electron transport layer (ETL), hole blocking layer (HBL), exciton blocking layer (EBL), hole transport layer (HTL), and/or hole injection layer (HIL). In addition to separate layers, some of these materials may be combined into a single layer. For example, a hole transport material and/or an electron transport material could be incorporated into the emissive layer.

In some embodiments, the light-emitting device can include an electron injection layer e.g., between the cathode layer and the light emitting layer. In some embodiments, the lowest un-occupied molecular orbital (LUMO) energy level of the material(s) that can be included in the electron injection layer is high enough to prevent it from receiving an electron from the light emitting layer. In other embodiments, the energy difference between the LUMO of the material(s) that can be included in the electron injection layer and the work function of the cathode layer is small enough to allow efficient electron injection from the cathode. A number of suitable electron injection materials are known to those skilled in the art. Examples of suitable material(s) that can be included in the electron injection layer include but are not limited to, an optionally substituted compound selected from the following: aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI) a triazine, a metal chelate of 8-hydroxyquinoline such as tris(8-hydroxyquinoliate) aluminum, and a metal thioxinoid compound such as bis(8-quinolinethiolato) zinc. In one embodiment, the electron injection layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

Some embodiments described herein can include an electron transport layer positioned between the cathode and light-emitting layer. Suitable electron transport materials are known to those skilled in the art. Exemplary electron transport materials that can be included in the electron transport layer are an optionally substituted compound selected from: aluminum tris(8-hydroxyquinolate) (Alq3), 2-(4-biphenylyl)-5-(4-tert-butylphenyl)-1,3,4-oxadiazole (PBD), 1,3-bis (N,N-t-butyl-phenyl)-1,3,4-oxadiazole (OXD-7), 3-phenyl-4-(1'-naphthyl)-5-phenyl-1,2,4-triazole (TAZ), 2,9-dimethyl-4,7-diphenyl-phenanthroline (bathocuproine or BCP), and 1,3,5-tris[2-N-phenylbenzimidazol-z-yl]benzene (TPBI). In one embodiment, the electron transport layer is aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

In some embodiments, the hole transport material is incorporated into the light-emitting layer. The amount of the electron transport material in the light-emitting layer may be from about 1% to about 99% by weight, or alternatively, from about 30% to about 70% by weight, of the light-emitting layer In some embodiments, the device can include a hole blocking layer, e.g., between the cathode and the light-emitting layer. Various suitable hole blocking materials that can be included in the hole blocking layer are known to those skilled in the art. Suitable hole blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton blocking layer, e.g., between the light-emitting layer and the anode. In one embodiment, the band gap of the material(s) that comprise exciton blocking layer is large enough to substantially prevent the diffusion of excitons. A number of suitable exciton blocking materials that can be included in the exciton blocking layer are known to those skilled in the art. Examples of material(s) that can compose an exciton blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole transport layer, e.g., between the light-emitting layer and the anode. Suitable hole transport materials that can be included in the hole transport layer are known those skilled in the art. For example, hole transport material(s) that can be included in the hole transport layer are 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4', 4''-tris(3-methylphenylphenylamino)triphenylamine (MTDATA), 4,4'-bis[N,N'-(3-tolyl)amino]-3,3'-dimethylbiphenyl (HMTPD), N,N'N''-1,3,5-tricarbazoloylbenzene (tCP), 4,4'-N,N'-dicarbazole-biphenyl (CBP), poly(9-vinylcarbazole) (PVK), 3,4,5-Triphenyl-1,2,3-triazole, 3,5-Bis(4-tert-butyl-phenyl)-4-phenyl[1,2,4]triazole, 2,9-Dimethyl-4,7-diphenyl-1,10-phenanthroline, 1,1-Bis(4-bis(4-methylphenyl)aminophenyl)cyclohexane, a carbazole, a polythiophene, a benzidine, N,N'-bis(4-butylphenyl)-N,N'-bis(phenyl)benzidine, a triphenylamine, a phenylenediamine, 4,4',4''-Tris(N-(naphthylen-2-yl)-N-phenylamino) triphenylamine, an oxadiazole, a polyacetylene and a phthalocyanine metal complex.

In some embodiments, the light-emitting device can include a hole injection layer, e.g., between the light-emitting layer and the anode. Various suitable hole injection materials that can be included in the hole injection layer are known to those skilled in the art. Exemplary hole injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4''-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), or a phthalocyanine metal complex derivative such as phthalocyanine copper. Hole-injection materials, while still being able to transport holes, may have a hole mobility substantially less than the hole mobility of conventional hole transport materials.

Those skilled in the art recognize that the various materials described above can be incorporated in several different layers depending on the configuration of the device. In one embodiment, the materials used in each layer are selected to result in the recombination of the holes and electrons in the light-emitting layer. An example of a device configuration that incorporates the various layers described herein is illustrated schematically in FIG. 1. The electron injection layer (EIL), electron transport layer (ETL), hole blocking layer (HBL), exciton blocking layer (EBL), hole transport layer (HTL), and hole injection layer (HIL) can be added to the light-emitting device using methods known to those skilled in the art (e.g., vapor deposition).

Light-emitting devices comprising the compounds or compositions disclosed herein can be fabricated using techniques known in the art, as informed by the guidance provided herein. For example, a glass substrate can be coated with a high work functioning metal such as ITO which can act as an anode. After patterning the anode layer, a light-emitting composition layer that includes a compound or a composition disclosed herein can be deposited on the anode. The cathode layer, comprising a low work functioning metal (e.g., Mg:Ag), can then be vapor evaporated onto the light-emitting composition layer. If desired, the device can also include an electron transport/injection layer, a hole blocking layer, a hole injection layer, an exciton blocking layer and/or a second light-emitting layer that can be added to the device using techniques known in the art, as informed by the guidance provided herein.

The light emitting devices described herein can be configured to emit various colors of light. For example, blue emitting compounds disclosed herein and orange emitting compound(s) can be placed in the light-emitting layer to produce white light.

Light-emitting devices comprising blue emitter compounds can be fabricated using techniques known in the art, as informed by the guidance provided herein. For example, a glass substrate can be coated with a high work functioning metal such as Indium Tin Oxide (ITO) which can act as an anode. After patterning the anode layer, a light-emitting composition layer that includes the blue emitting compound can be deposited on the anode. The cathode layer, comprising a low work functioning metal (e.g., Mg:Ag), can then be vapor evaporated onto the light-emitting composition layer. If desired, the device can also include an electron transport/injection layer, a hole blocking layer, a hole injection layer, an exciton blocking layer and/or a second light-emitting layer that can be added to the device using techniques known in the art.

EXAMPLES

Example 1

General Synthetic Methods

While there are many ways readily apparent to those skilled in the art to prepare the compounds disclosed, general Scheme 1 illustrates a method that can be used to prepare a variety of compounds.

In this method, a phenyl substituted phenyl ring (compound 1) having an amine or hydroxyl moiety (—X—H) para to a halogen such as —I, is coupled to $R^2$ using a catalyst such as a base (e.g. $K_2CO_3$) to form compound 2. Compound 2 is then coupled to a protected acetylene, via a halogen-metal coupling reaction. The acetylene is then deprotected to yield compound 3. The deprotected acetylene is then coupled to the second aromatic ring (i.e. R1) via a second halogen-metal coupling to form compound 4. A variety of substitution is available the aryl rings via precursor compounds which are readily purchased or prepared using standard reactions. Finally, a variety of $R^1$—Br are available via commercially available compounds and standard chemistry.

Scheme 2

Example 1

4-Bromo-3,5-dimethylphenol (10.05 g, 50.0 mmol) and K₂CO₃ (9.0 g, 65.2 mmol) was stirred for 10 minutes in DMF (25 mL). 2-Bromo-(2-methoxyethoxy)-ethane was added, and the reaction mixture was heated at 45° C. overnight under argon. After cooling to room temperature, the reaction mixture was poured into ~300 mL DCM; filtered off white solids. Flash column (silica; 100% hexane) gave 12.95 g (85% yield) of product 6.

Pd₂(dba)₃ (600 mg) and CuI (600 mg) were added to 1,4-dioxane (75 mL), and the mixture was degassed for 20 minutes. P(t-Bu)₃ (24 mL; solution as 10% in hexanes) was added, and degassing continued for 10 minutes. 4-Bromo-3,5-dimethyl-1-(2-(2-methoxyethoxy)ethoxy)benzene (6) (12.95 g, 42.7 mmol) and triisopropylsilylacetylene (31.09 g, 171 mmol) were added; and degassing was continued for 15 minutes. Diisopropylamine (18 mL) was added, and reaction mixture was further degassed for 20 minutes. The mixture was heated at 90° C. for 36 hours under argon. The mixture was removed from heat, cooled, poured into ~200 mL of diethyl ether, and grey solids formed were filtered off. The filtrate was purified by flash column (silica; 100% hexane to 10% ethyl acetate in hexane gradient) to give 13.20 g of product 7 (76% yield).

15

8

9

3,5-dimethyl-1-(2-(2-methoxyethoxy)ethoxy)-phenyl-tri-isopropylsilylacetylene (7) (13.20 g, 32.7 mmol) was added to THF (50 mL) and solution was cooled to 0° C. Tetrabutylammonium fluoride (38 mL of 1M solution, 38 mmol) was then added slowly to the solution. The solution was removed from the ice bath and stirred at room temperature for 70 minutes. The solution was then poured into 300 mL of saturated ammonium chloride solution, and extracted twice with diethyl ether (150 mL). The organic layer was dried with sodium sulfate. Flash column (silica; 100% hexane to 12% ethyl acetate in hexane gradient) gave 7.45 g of product 8 (~92%).

Pd$_2$(dba)$_3$ (250 mg) and CuI (250 mg) were added to 1,4-dioxane (20 mL). The mixture was degassed for 20 minutes, P(t-Bu)$_3$ (12 mL; solution as 10% in hexanes) was added, and degassing continued for 10 minutes. 3,5-dimethyl-1-(2-(2-methoxyethoxy)ethoxy)-phenylacetylene (8) (4.0 g, 16.0 mmol) and 4-bromo-2,6-difluorobenzonitrile (2.98 g, 13.7 mmol) were then added, and degassing continued for another 10 minutes. Diisopropylamine (7.2 mL) was then added, and the reaction mixture was further degassed for 20 minutes. The reaction mixture was then heated at 68° C. overnight under argon. The mixture was then cooled and poured into THF (200 mL), filtered, and the solids were washed with additional THF. The combined filtrates were purified by flash column (silica; 5% to 30% ethyl acetate in hexane gradient) to give 4.44 g of product 9 (84% yield).

16

Scheme 3

5

10

11

12

13

Example 2

10

A mixture of 4-bromo-3,5-dimethylphenol (4.0 g, 19.9 mmol) and $K_2CO_3$ (4.14 g, 30.0 mmol) was stirred in DMF (15 mL) for 10 minutes. Iodomethane (5.76 g, 40.0 mmol) was added and the reaction mixture was heated at 35° C. for 23 hours under argon. After cooling, the mixture was poured into DCM (150 mL) and white solids were filtered off. Filtrate was purified by flash column (silica; 100% hexane) to give 2.79 g of product 10 (65% yield).

11

$Pd_2(dba)_3$ (150 mg) and CuI (150 mg) were added to 1,4-dioxane (15 mL). The mixture was degassed for 20 minutes, 2,6-dimethyl-4-methoxybromobenzene (10) (2.60 g, 12.1 mmol) and triisopropylsilylacetylene (9.43 g, 51.7 mmol) were added, and degassing continued for 10 minutes. Diisopropylamine (4.5 mL) was then added, and the reaction mixture was degassed for 20 minutes. The mixture was heated at 90° C. overnight under argon, cooled, and then poured into diethyl ether (100 mL) and filtered. Flash column (silica; 100% hexane) gave 3.59 g of product 11 (94% yield).

12

3,5-dimethyl-1-methoxyphenyltriisopropylacetylene (11) (3.50 g, 11.1 mmol) in THF (20 mL) was cooled to 0° C., and tetrabutylammonium fluoride (15 mL of 1M solution, 15 mmol) was slowly added. The solution was removed from ice bath, stirred at room temperature for 60 minutes under argon, and then poured into 300 mL of saturated ammonium chloride solution, and extracted twice with diethyl ether (100 mL). Flash column (silica; 100% hexane) gave 1.47 g of product 12 (83% yield).

13

$Pd_2(dba)_3$ (100 mg) and CuI (100 mg) were added to 1,4-dioxane (15 mL). The mixture was degassed for 20 minutes, $P(t-Bu)_3$ (4 mL; solution as 10% in hexanes) was added, and degassing continued 10 minutes. 3,5-dimethyl-1-methoxyphenylacetylene (12) (1.4 g, 8.8 mmol) and 4-bromo-2,6-difluorobenzonitrile (1.74 g, 8.0 mmol) were then added and degassing continued for 10 min. Diisopropylamine (2.5 mL) was then added and the reaction mixture was degassed an additional 20 minutes. The mixture was then heated at 68° C. overnight under argon. The mixture was then cooled, poured it into THF (150 mL), and filtered. The filtrate was purified by flash column (silica; 100% hexane to 4% ethyl acetate in hexane gradient) to give 1.96 g of crude material. After vacuum sublimation, 1.65 g of product 13 was isolated (69% yield).

Scheme 4

14

-continued utes. P(t-Bu)$_3$ (4 mL; solution as 10% in hexanes) was then added, and degassing continued 10 minutes. Next, 2,6-dimethyl-4-(2-ethylhexoxy)iodobenzene (14) (1.5 g, 4.2 mmol) and triisopropylsilylacetylene (3.04 g, 16.7 mmol) were added and degassing continued 10 minutes. Finally, diisopropylamine (2.5 mL) was added and reaction mixture was degassed for 20 minutes. The mixture was then heated at 90° C. overnight under argon. After cooling, the reaction mixture was poured into diethyl ether (100 mL) and filtered. Filtrate was purified by flash column (silica; 100% hexane) to give 1.52 g of product 15 (88% yield).

3,5-dimethyl-1-(2-ethylhexoxy)phenyltriisopropylsilylacetylene (15) (1.45 g, 3.50 mmol) in THF (10 mL) was cooled to 0° C., and tetrabutylammonium fluoride (4 ml of 1M solution, 4 mmol) was slowly added. The solution was then removed from the ice bath and stirred at room temperature for 60 minutes under argon. The solution was then poured into 150 mL of saturated ammonium chloride solution and extracted with diethyl ether (3×100 mL). Flash column (silica; 100% hexane) gave 800 mg of product 16 (84% yield).

Example 3

Pd$_2$(dba)$_3$ (100 mg) and CuI (100 mg) were added to 1,4-dioxane (15 mL), and the mixture was degassed for 20 min-

Pd$_2$(dba)$_3$ (70 mg) and CuI (70 mg) were added to 1,4-dioxane (15 mL), and the mixture was degassed for 20 minutes. P(t-Bu)$_3$ (3 mL; solution as 10% in hexanes) was then added, and degassing continued 10 minutes. 3,5-dimethyl-1-(2-ethylhexoxy)phenylacetylene (16) (790 mg, 2.7 mmol) and 4-bromo-2,6-difluorobenzenonitrile (525 mg, 2.4 mmol) were then added and degassing continued for 10 minutes. Diisopropylamine (2 mL) was then added and the reaction mixture was degassed for 20 minutes. Next, the mixture was heated at 68° C. overnight under argon. After cooling, reaction mixture was poured into THF (100 mL) and filtered.

Filtrate was purified by flash column (silica; 2% to 25% DCM in hexane gradient). Recrystallization in DCM/MeOH gave 730 mg of product 17 (74% yield).

Scheme 5

Example 4

Pd$_2$(dba)$_3$ (75 mg) and CuI (75 mg) were added to 1,4-dioxane (20 mL), and the mixture was degassed for 20 minutes. P(t-Bu)$_3$ (3 mL; solution as 10% in hexanes) was then added, and degassing continued 10 minutes. 3,5-dimethyl-1-(2-(2-methoxyethoxy)ethoxy)-phenylacetylene (8) (1.0 g, 4.0 mmol) and 4-bromo-2,3,5,6-tetrafluorobenzenonitrile (886 mg, 3.5 mmol) were then added, degassing was continued for 10 minutes. Diisopropylamine (2 mL) was then added, and the reaction mixture was further degassed for 20 minutes. The reaction mixture was then heated at 68° C. overnight under argon. After heating, the mixture was cooled, then poured into THF (150 mL) and filtered. Filtrate was purified by flash column (silica; 10% to 50% ethyl acetate in hexane gradient) to give 147 mg of product 18 (9% yield).

Scheme 6

Example 5

2,4,6-trimethoxybenzaldehyde (10.0 g, 51 mmol) and bromomethyltriphenylphosphonium bromide (24.45 g, 56 mmol) in THF (200 mL) were cooled to 0° C., and potassium tert-butoxide (66 mL of 1M solution, 66 mmol) was slowly added. The reaction mixture was stirred overnight while slowly warming to room temperature. Flash column (silica; 10% to 20% ethyl acetate in hexane gradient) gave 9.3 g of product 19 (67% yield).

20

2-(2-bromoethenyl)-1,3,5-trimethoxybenzene (19) (9.27 g, 33.9 mmol) was dissolved in THF (200 mL) and potassium tert-butoxide (70 mL of 1M solution, 70 mmol) was slowly added. The reaction mixture was then heated under reflux (90° C.) for two hours. After cooling, the KBr salt were filtered from the reaction mixture, and washed with additional THF (50 mL). All filtrates were then combined, and purified by flash column (silica; 20% ethyl acetate in hexane) to give 3.84 g of product 20 (59% yield).

21

Pd$_2$(dba)$_3$ (150 mg) and CuI (150 mg) were added to 1,4-dioxane (30 mL) and the mixture was degassed for 20 minutes. P(t-Bu)$_3$ (6 mL; solution as 10% in hexanes) was then added, and degassing continued 10 minutes. 2,4,6-trimethoxyphenylacetylene (20) (2.0 g, 10.4 mmol) and 4-bromo-2,6-difluorobenzonitrile (2.13 g, 9.8 mmol) were next added and degassing continued for 10 minutes. Diisopropylamine (4.5 mL) was then added, and reaction mixture was further degassed for 20 minutes. The reaction mixture was then heated at 68° C. overnight under argon. After heating, the mixture was cooled, and then poured into THF (250 mL) and filtered. A flash column done with the filtrate (silica; 10% to 50% ethyl acetate in hexane gradient) gave 1.45 g of product 21 (45% yield).

Scheme 7

25

Example 6

22

To a mixture of 4-iodoanisole (5.0 g, 21.4 mmol), 4-bromo-3,5-dimethylphenol (6.44 g, 32.1 mmol), cesium carbonate (13.95 g, 42.8 mmol) and dimethylglycine hydrochloride (896 mg, 6.42 mmol) was added 1,4-dioxane (25 mL). The freeze-thaw method (2 cycles) was used to purge the mixture. Copper Iodide (407 mg, 2.14 mmol) was then added to the mixture, and freeze-thaw (3 cycles) was continued. The reaction mixture was then heated at 120° C. overnight. After cooling, the mixture was poured into ethyl acetate (200 mL) and washed with water and brine. Flash column (silica; 100% hexane to 1% ethyl acetate in hexane gradient) gave 3.05 g of product 22 (46% yield).

23

Pd$_2$(dba)$_3$ (250 mg) and CuI (250 mg) were added to 1,4-dioxane (35 mL), and the mixture was degassed for 20 minutes. P(t-Bu)$_3$ (12 mL; solution as 10% in hexanes) was added, and degassing continued 10 minutes. 1-Bromo-2,6-dimethyl-4-(4-methoxyphenoxy)benzene (22) (3.90 g, 12.66 mmol) and triisopropylsilylacetylene (9.24 g, 50.6 mmol) were then added and degassing continued for 10 minutes. Diisopropylamine (7.5 mL) was added next, and reaction mixture was further degassed for 20 minutes. The reaction mixture was then heated at 90° C. overnight under argon. The mixture was cooled, then poured into diethyl ether (200 mL) and filtered. A flash column of the filtrate (silica; 2% to 5% ethyl acetate in hexane gradient) gave 4.97 g of product 23 (96% yield).

24

2,6-dimethyl-4-(4-methoxyphenoxy)phenyltriispropylsilylacetylene (23) (4.8 g, 11.7 mmol) in THF (25 mL) was cooled to 0° C., and tetrabutylammonium fluoride (15 mL of 1M solution, 15 mmol) was slowly added. The solution was then removed from the ice bath and stirred at room temperature for 1.5 hours. After stirring, the solution was poured into saturated ammonium chloride solution (250 mL) and extracted with diethyl ether (3 times 150 mL). Flash column (silica; 2% TO 5% ethyl acetate in hexane gradient) gave 2.22 g of product 24 (75% yield).

25

Pd$_2$(dba)$_3$ (150 mg) and CuI (150 mg) were added to 1,4-dioxane (20 mL) and the mixture was degassed for 20 minutes. P(t-Bu)$_3$ (6 mL; solution as 10% in hexanes) was then added, and degassing continued for 10 minutes. Next, 2,6-dimethyl-4-(4-methoxyphenoxy)phenylacetylene (24) (1.5 g, 5.9 mmol) and 4-bromo-2,6-difluorobenzenonitrile (1.18 g, 5.4 mmol) were added and degassing was continued for 10 minutes. Diisopropylamine (4.5 mL) was then added, and reaction mixture was further degassed for 20 minutes. The reaction mixture was then heated at 68° C. overnight under argon. After heating, the mixture was cooled, then poured into THF (200 mL) and filtered. A flash column of the filtrate (silica; 2% to 10% ethyl acetate in hexane gradient) and two recrystallizations in DCM/hexane and DCM/MeOH gave 1.58 g of product 25 (75% yield).

Example 7

Device Fabrication

Fabrication of light-emitting device: the ITO coated glass substrates were cleaned by ultrasound in acetone, and consecutively in 2-propanol, baked at 110° C. for 3 hours, followed by treatment with oxygen plasma for 5 min. A layer of PEDOT: PSS (Baytron P purchased from H.C. Starck) was spin-coated at 3000 rpm onto the pre-cleaned and O$_2$-plasma treated (ITO)-substrate and annealed at 180° C. for 10 min, yielding a thickness of around 40 nm. In a glove-box hosted vacuum deposition system at a pressure of 10$^{-7}$ torr (1 torr=133.322 Pa), 4,4'4"-tri(N-carbazolyl)triphenylamine (TCTA) was first deposited on top of PEDOT/PSS layer at deposition rate of 0.06 nm/s, yielding a 30 nm thick film. Then 4,4'-bis(carbazol-9-yl)biphenyl (CBP) and deep blue emitter compound 9 were concurrently heated and deposited on top of TCTA under different deposition speed to make 9 at 3 wt %, followed by deposition of 1,3,5-tris(N-phenylbenzimidizol-2-yl)benzene (TPBI) at deposition rate around 0.06 nm/s. CsF and Al were then deposited successively at deposition rates of 0.005 and 0.2 nm/s, respectively. Each individual device has areas of 0.14 cm$^2$.

Example 8

Device Performance

Figure 1:
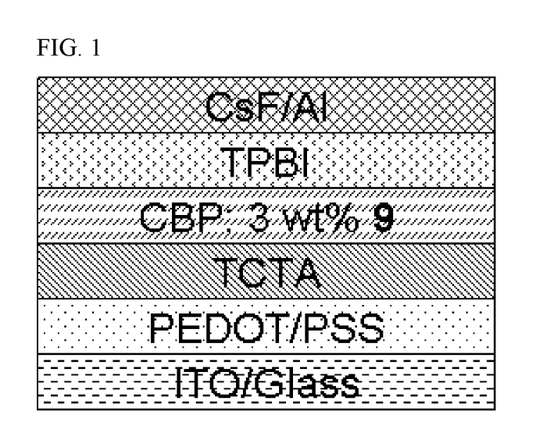
FIG. 1 shows an exemplary configuration of an organic light-emitting device incorporating an embodiment of deep blue emissive compound of Formula 1.
Figure 2:
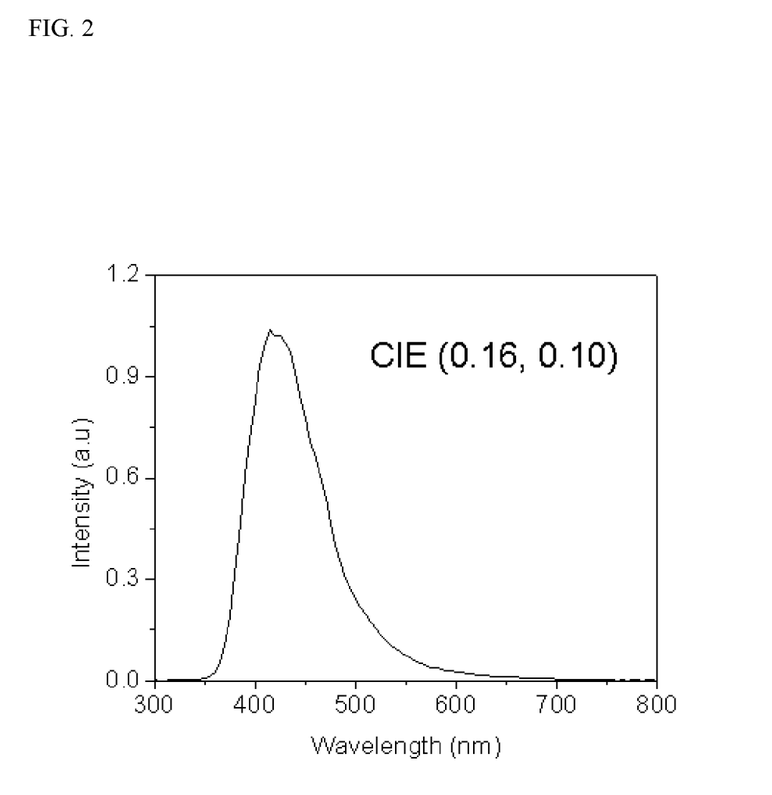
FIG. 2 is a graph depicting the emissive spectrum and CIE coordinates of an embodiment of an organic light-emitting device of FIG. 1.
Figure 3:
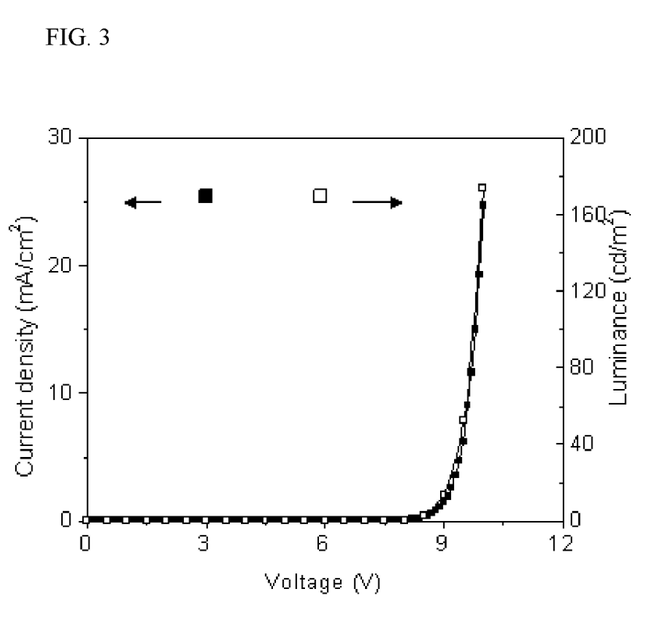
FIG. 3 is a graph depicting the current density and luminance of an embodiment of a device of FIG. 1 as a function of the driving voltage.
Figure 4:
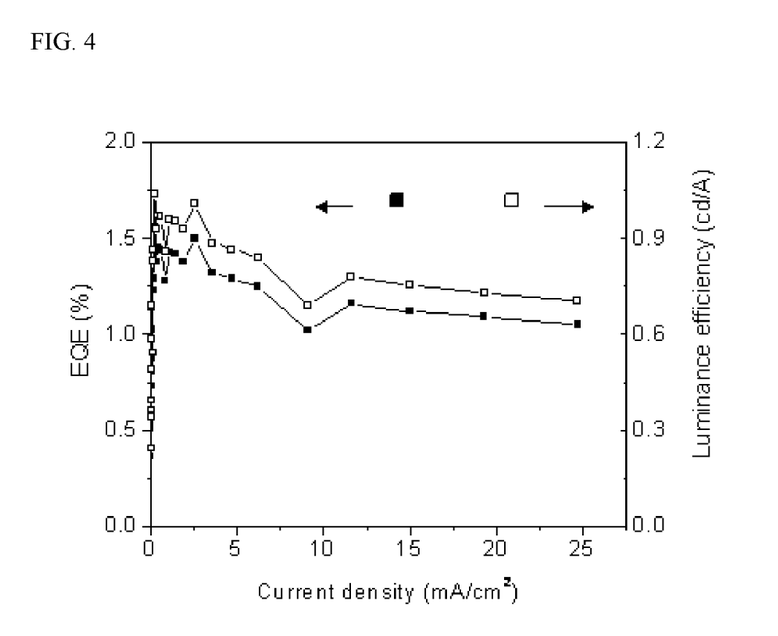
FIG. 4 is a graph depicting the External Quantum Efficiency (EQE) and luminous efficiency of an embodiment of a device of FIG. 1, as a function of current density.

Device A, comprising Compound 9 and fabricated in accordance with Examples 1 and 2, was tested to determine the emissive qualities of the device by examining the (1) emissive intensity of Device A (intensity of the device [a.u.] as a function of wavelength; (2) determining the CIE coordinates of Device A; and (3) determining the efficiency of Device A (current density and luminescence as a function of the voltage applied to the device; and external quantum efficiency and luminescence as a function of current density). All spectra were measured with an Ocean Optics HR 4000 spectrometer (Ocean Optics, Dunedin, Fla., USA) and 1-V-L characteristics were taken with a Keithley 2400 SourceMeter (Keithley Instruments, Inc., Cleveland, Ohio, USA) and Newport 2832-C power meter and 818 UV detector (Newport, Corp., Irvine, Calif., USA). All device operation was performed inside a nitrogen-filled glove-box. An exemplary configuration of the device (Device A) is shown in FIG. 1. FIG. 2 shows electroluminescence spectrum of Device A, plus the CIE coordinate. The spectrum shows significant emission between 400 and 500 nm. The purity of the deep blue emitted radiation is demonstrated by the CIE coordinates (X=0.16; Y=0.10). In addition, as shown in FIGS. 3 and 4, Device A demonstrates efficacy in conventional organic light emitting device parameters. Thus Compound 9 has demonstrated its effectiveness as a blue emitting compound in organic light emitting devices.

What is claimed is:

1. A compound represented by a formula:

wherein R$^2$ is C$_{1-30}$ alkyl, or C$_{1-30}$O$_{1-15}$ ether;
R$^3$ and R$^4$ are independently selected from —H, —F, —Cl, —Br, —I, C$_{1-10}$ alkyl, C$_{1-10}$O ether, and optionally substituted C$_{6-10}$ aryl;
R$^5$ and R$^6$ are independently selected from —F, —Cl, —Br, —I, C$_{1-10}$ alkyl, C$_{1-10}$O ether, and optionally substituted C$_{6-10}$ aryl;
X is —O— or —NR$^7$—, wherein R$^7$ is —H, C$_{1-12}$ alkyl, or C$_{1-12}$O$_{1-6}$ ether;
R$^8$ and R$^9$ are independently —H, —F, —Cl, —Br, —I, C$_{1-10}$ alkyl or C$_{1-10}$ ether; and
R$^{10}$, R$^{11}$ and R$^{12}$ are independently halogen, —CN, or —NO$_2$.

2. The compound of claim 1, wherein R$^{12}$ is —CN.

3. The compound of claim 1, wherein R$^{10}$ and R$^{11}$ are —F.

4. The compound of claim 1, wherein R$^2$ is C$_{1-12}$ alkyl or C$_{1-9}$O$_{1-4}$ ether.

5. The compound of claim 1, wherein R$^2$ is

6. The compound of claim 1, wherein R$^3$ and R$^4$ are independently selected from: —H, —F, —Cl, —Br, —I, C$_{1-4}$ alkyl, and C$_{1-4}$O ether; and R$^5$ and R$^6$ are independently selected from: —F, —Cl, —Br, —I, C$_{1-4}$ alkyl, and C$_{1-4}$O ether.

7. The compound of claim 1, wherein R$^5$ and R$^6$ are independently —CH$_3$, isopropyl, or —OCH$_3$.

8. The compound of claim 1, selected from:

-continued

-continued

9. A light-emitting device, comprising:
an anode layer;
a cathode layer; and
a light-emitting layer positioned between the anode layer and the cathode layer, the light-emitting layer comprising a compound represented by a formula:

wherein $R^2$ is $C_{1-30}$ alkyl, or $C_{1-30}O_{1-15}$ ether;

$R^3$ and $R^4$ are independently selected from —H, —F, —Cl, —Br, —I, $C_{1-10}$ alkyl, $C_{1-10}O$ ether, and optionally substituted $C_{6-10}$ aryl;

$R^5$ and $R^6$ are independently selected from —F, —Cl, —Br, —I, $C_{1-10}$ alkyl, $C_{1-10}O$ ether, and optionally substituted $C_{6-10}$ aryl;

X is —O— or —NR$^7$—, wherein $R^7$ is —H, $C_{1-12}$ alkyl, or $C_{1-12}O_{1-6}$ ether;

$R^8$ and $R^9$ are independently —H, —F, —Cl, —Br, —I, $C_{1-10}$ alkyl or $C_{1-10}$ ether; and $R^{10}$, $R^{11}$ and $R^{12}$ are independently halogen, —CN, or —NO$_2$.

10. The device of claim 9, wherein $R^{10}$ and $R^{11}$ are independently —F, —Cl, or —Br.

11. The device of claim 9, wherein $R^{12}$ is —CN.

12. The device of claim 9, wherein $R^2$ is $C_{4-30}$ alkyl.

13. The device of claim 9, wherein $R^2$ is $C_{1-9}O_{1-4}$ ether.

14. The device of claim 9, wherein X is —O—.

15. The device of claim 9, wherein X is —NR$^7$—.

* * * * *